(12) United States Patent
Michaels et al.

(10) Patent No.: US 8,861,673 B2
(45) Date of Patent: Oct. 14, 2014

(54) COMPONENT APERTURE LOCATION USING COMPUTED TOMOGRAPHY

(75) Inventors: Derek J. Michaels, Vernon, CT (US); Rodney H. Warner, Austin, TX (US)

(73) Assignee: United Technologies Corporation, Hartford, CT (US)

( * ) Notice: Subject to any disclaimer, the term of this patent is extended or adjusted under 35 U.S.C. 154(b) by 370 days.

(21) Appl. No.: 13/307,458

(22) Filed: Nov. 30, 2011

(65) Prior Publication Data
US 2013/0136225 A1    May 30, 2013

(51) Int. Cl.
*A61B 6/00* (2006.01)
(52) U.S. Cl.
USPC .................................................. 378/4
(58) Field of Classification Search
CPC ............ A61B 6/032; A61B 6/02; A61B 6/03; G06T 11/006; G06T 11/005; G06T 15/00; G06T 17/00
USPC ...................................... 378/4, 901
See application file for complete search history.

(56) References Cited

U.S. PATENT DOCUMENTS

| | | | | |
|---|---|---|---|---|
| 2,116,637 A | * | 5/1938 | Niemann | 378/154 |
| 4,983,841 A | | 1/1991 | Stewart et al. | |
| 5,848,115 A | * | 12/1998 | Little et al. | 378/4 |
| 6,153,889 A | | 11/2000 | Jones | |
| 6,977,356 B2 | | 12/2005 | Vaidyanathan et al. | |
| 7,092,484 B1 | | 8/2006 | Jensen et al. | |
| 7,602,963 B2 | | 10/2009 | Nightingale et al. | |
| 2009/0248355 A1 | | 10/2009 | Kriegmair | |
| 2011/0185572 A1 | | 8/2011 | Wei et al. | |

FOREIGN PATENT DOCUMENTS

| | | |
|---|---|---|
| EP | 0875751 | 11/1998 |
| EP | 2312122 | 4/2011 |
| EP | 2385214 | 11/2011 |
| JP | 3151501 | 6/1991 |

OTHER PUBLICATIONS

European Search Report for EP Application 12194874, completed Mar. 11, 2013.
Carmignato S et al, Testing of x-ray microtomography systems using a traceable geometrical standard, Measurement Science and Technology, IOP, Bristol, GB, vol. 20, No. 8, Aug. 1, 2009.
Marinello F et al, "Calibration artefact for the microscale with high aspect ration: the fiber gauge", Cirp Annals, Elsevier BV, NL, CH, FR, vol. 57, No. 1, Jan. 1, 2008.
Gerhard Schick, "Metrology CT technology and its applications in the precision engineering industry", Proceedings of Spie, vol. 7522, Dec. 4, 2009.
Kruth J P et al, "Computed tomography for dimensional metrology", Cirp Annals, vol. 60, No. 2, 2011.

* cited by examiner

*Primary Examiner* — Jurie Yun
(74) *Attorney, Agent, or Firm* — Carlson, Gaskey, & Olds, P.C.

(57) ABSTRACT

An exemplary component measuring method includes determining a position of an aperture of a component using a computed tomography scan of a gage and a component. The gage is inserted into the aperture of the component during the computed tomography scan.

22 Claims, 5 Drawing Sheets

COMPONENT APERTURE LOCATION USING COMPUTED TOMOGRAPHY

BACKGROUND

This disclosure relates to locating apertures within a component and, more particularly, to using computed tomography scans to locate the apertures.

It is often desirable to determine the dimensions of a physical component. The dimensions are used to create a computer model of the physical component, for example. Many measurement techniques have developed for determining such dimensions. Some components have relatively complex features and geometries, which makes determining dimensions difficult.

Turbomachines, such as gas turbine engines, are well known. Turbomachines typically include a compressor that compresses air and delivers it downstream into a combustion section. The compressed air is mixed with fuel and combusted. The products of combustion pass downstream through a turbine. The compressor and turbine each include rotors. Arrays of removable blades are mounted to the rotors. The blades include apertures used to communicate cooling fluid to the outwardly facing surfaces of the blades.

Turbomachine components are one example component having relatively complex geometries. Determining the dimensions of the apertures in the blades is particularly difficult.

SUMMARY

An exemplary component measuring method includes determining a position of an aperture of a component using a computed tomography scan of a gage and a component. The gage is inserted into the aperture of the component during the computed tomography scan.

Another exemplary component measuring method includes inserting a plurality of gages into respective apertures of a component. The method then uses computed tomography scanning of the gages and the component to determine the positions of the apertures.

An exemplary component measuring system includes a controller module that determines a position of an aperture within a component using a computed tomography scan of the component and a gage inserted into the aperture.

DESCRIPTION OF THE FIGURES

The various features and advantages of the disclosed examples will become apparent to those skilled in the art from the detailed description. The figures that accompany the detailed description can be briefly described as follows.

DETAILED DESCRIPTION

Figure 1:
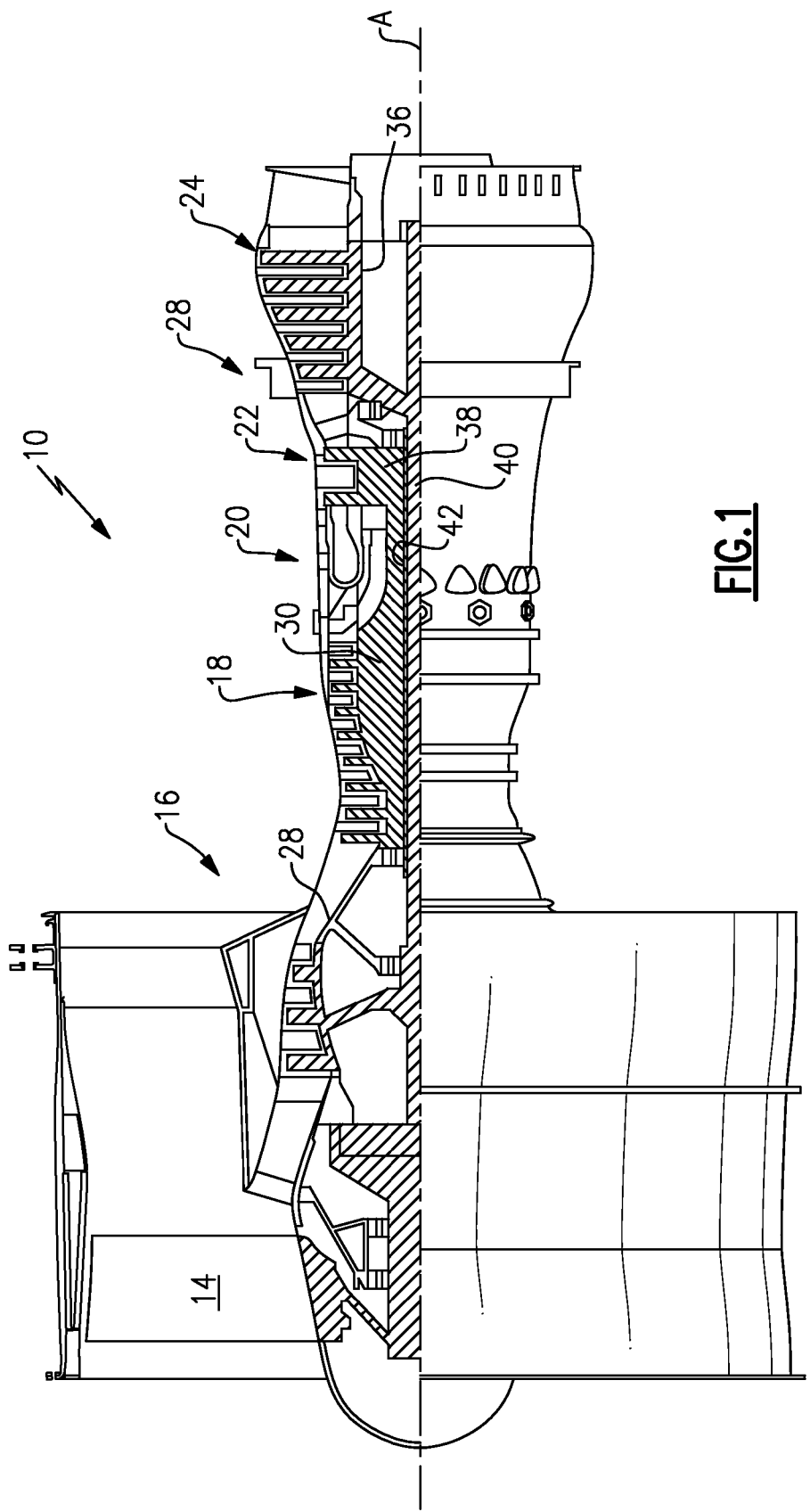
FIG. 1 shows a section view of an example turbomachine.

Referring to FIG. 1, an example turbomachine, such as a gas turbine engine 10, is circumferentially disposed about an axis A. The gas turbine engine 10 includes a fan 14, a low-pressure compressor section 16, a high-pressure compressor section 18, a combustion section 20, a high-pressure turbine section 22, and a low-pressure turbine section 24. Other example turbomachines may include more or fewer sections.

During operation, air is compressed in the low-pressure compressor section 16 and the high-pressure compressor section 18. The compressed air is then mixed with fuel and burned in the combustion section 20. The products of combustion are expanded across the high-pressure turbine section 22 and the low-pressure turbine section 24.

The low-pressure compressor section 16 and the high-pressure compressor section 18 each include rotors 28 and 30, respectively. The example rotors 28 and 30 include alternating rows of rotatable blades and static blades.

The high-pressure turbine section 22 and the low-pressure turbine section 24 each include rotors 36 and 38, respectively. The example rotors 36 and 38 include alternating rows of rotatable blades and static blades.

The rotors 36 and 38 rotate in response to the expansion to rotatably drive rotors 28 and 30. The rotor 36 is coupled to the rotor 28 with a spool 40, and the rotor 38 is coupled to the rotor 30 with a spool 42.

The examples described in this disclosure is not limited to the two-spool gas turbine architecture described, and may be used in other architectures, such as a single-spool axial design, a three-spool axial design, and still other architectures. That is, there are various types of gas turbine engines, and other turbomachines, that can benefit from the examples disclosed herein.

Figure 2:
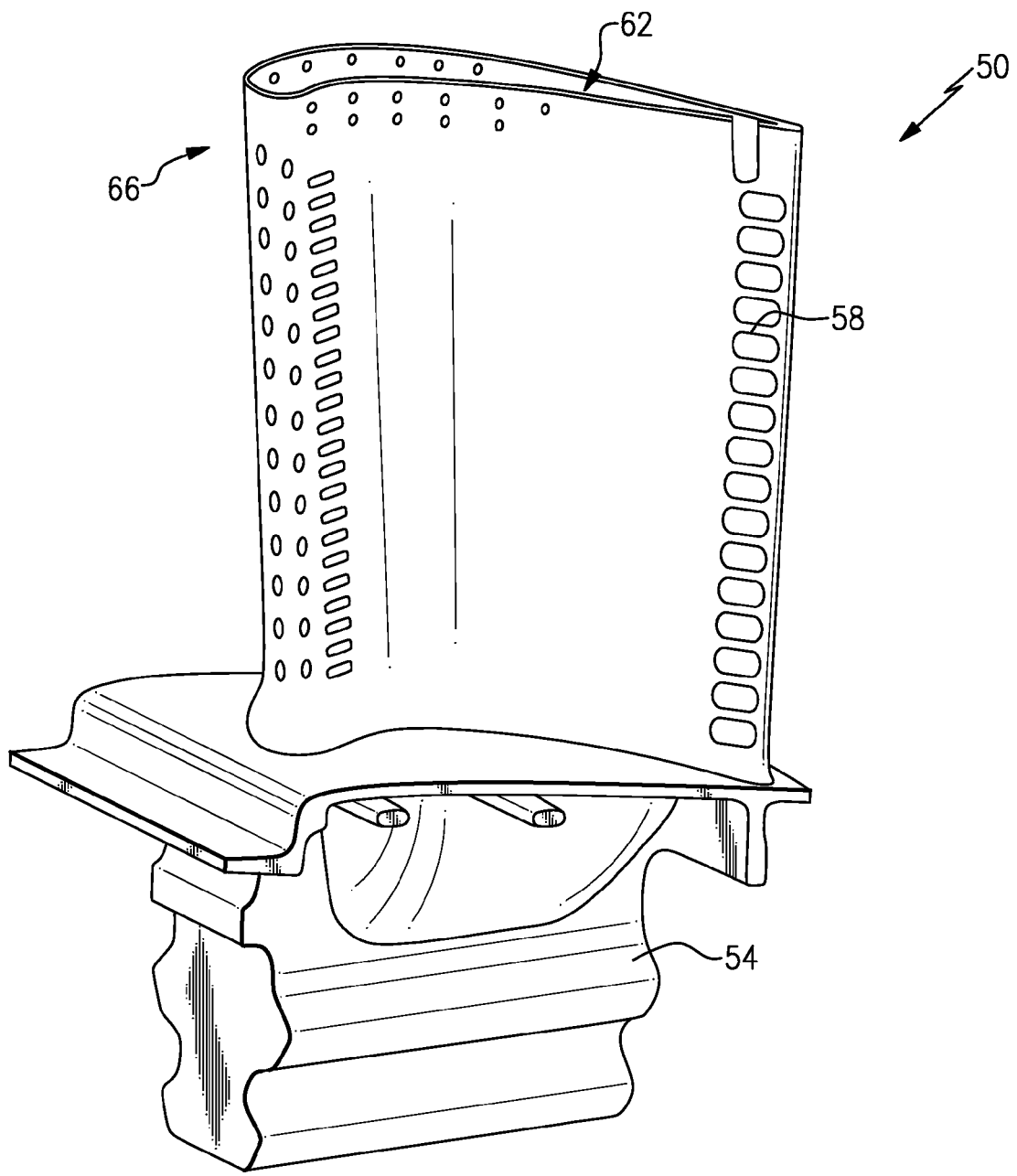
FIG. 2 shows a perspective view of a blade from the FIG. 1 turbomachine.

Referring to FIG. 2, a blade 50 of the FIG. 1 turbomachine includes a root 54 and an airfoil portion 58 extending from the root 54. The airfoil portion 58 includes a plurality of cooling holes 62. The cooling holes 62 are apertures and are, in this example, concentrated near a radial tip 66 of the airfoil portion 58.

Passages (not shown) through the airfoil portion 58 communicate a cooling fluid from a cavity within the blade 50 to the cooling holes 62. The cooling fluid cools the blade 50. The diameters and orientations of the passages and the cooling holes 62 may vary, as is known.

Figure 3:
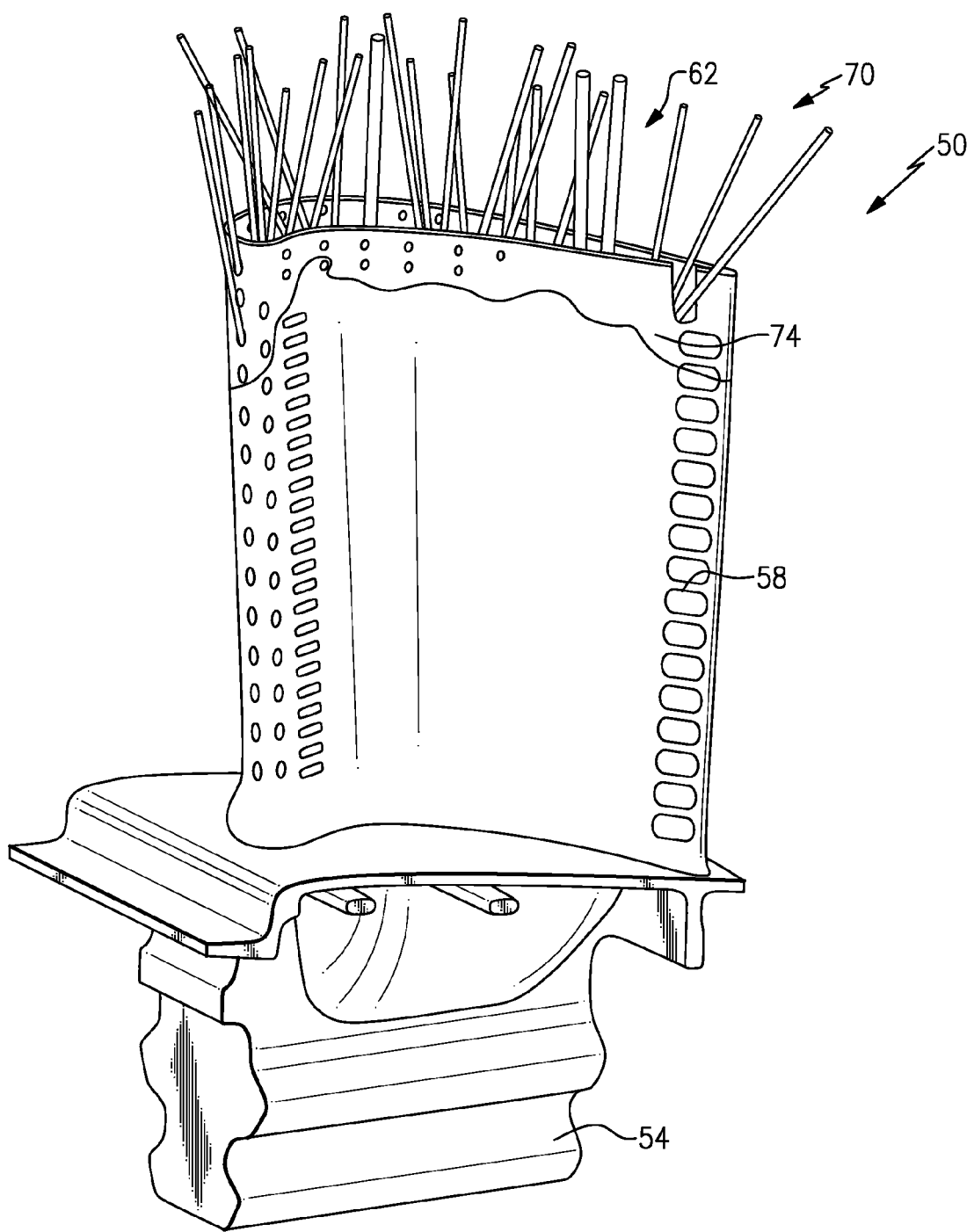
FIG. 3 shows a perspective view of the FIG. 2 blade with gage pins inserted into cooling holes of the FIG. 2 blade.
Figure 4:
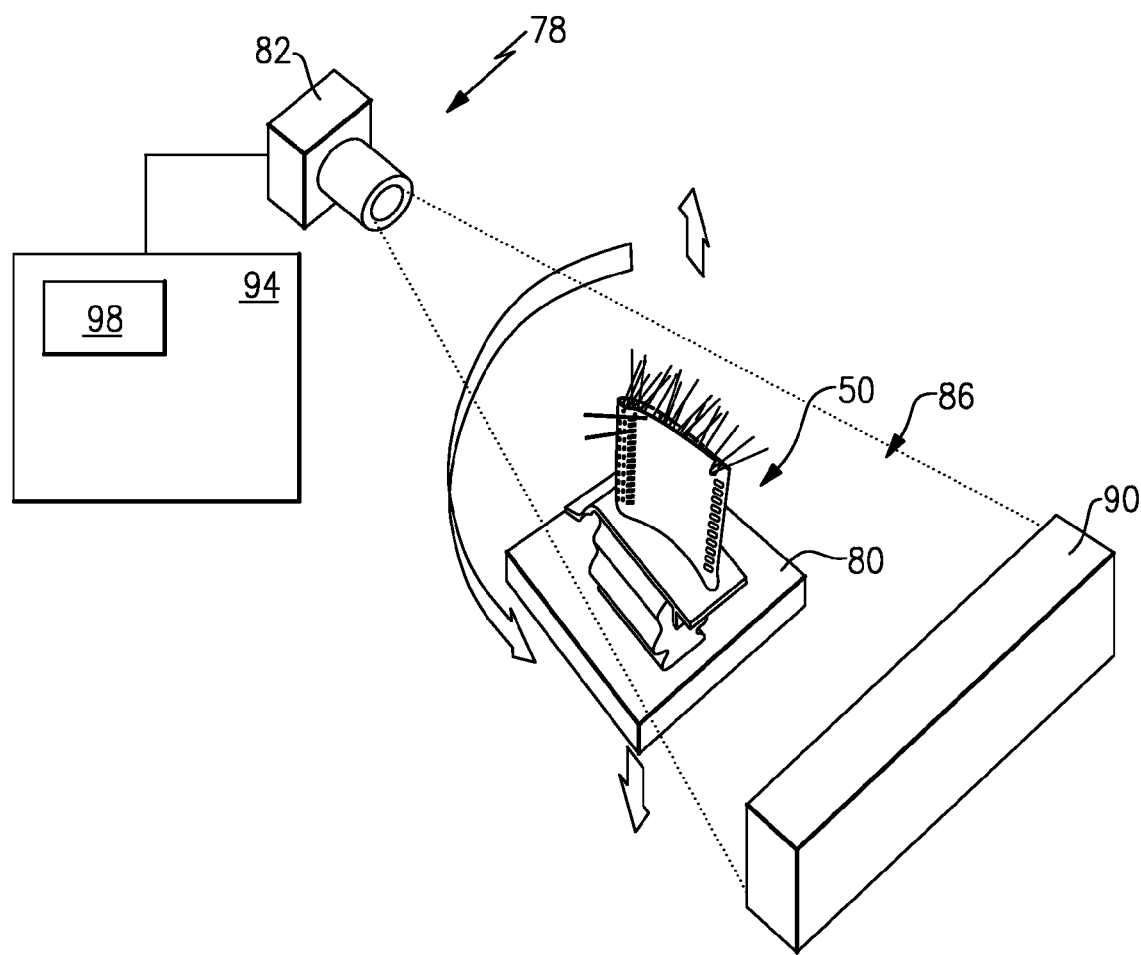
FIG. 4 shows a partially schematic view of the FIG. 3 blade during a computed tomography scan.
Figure 5:
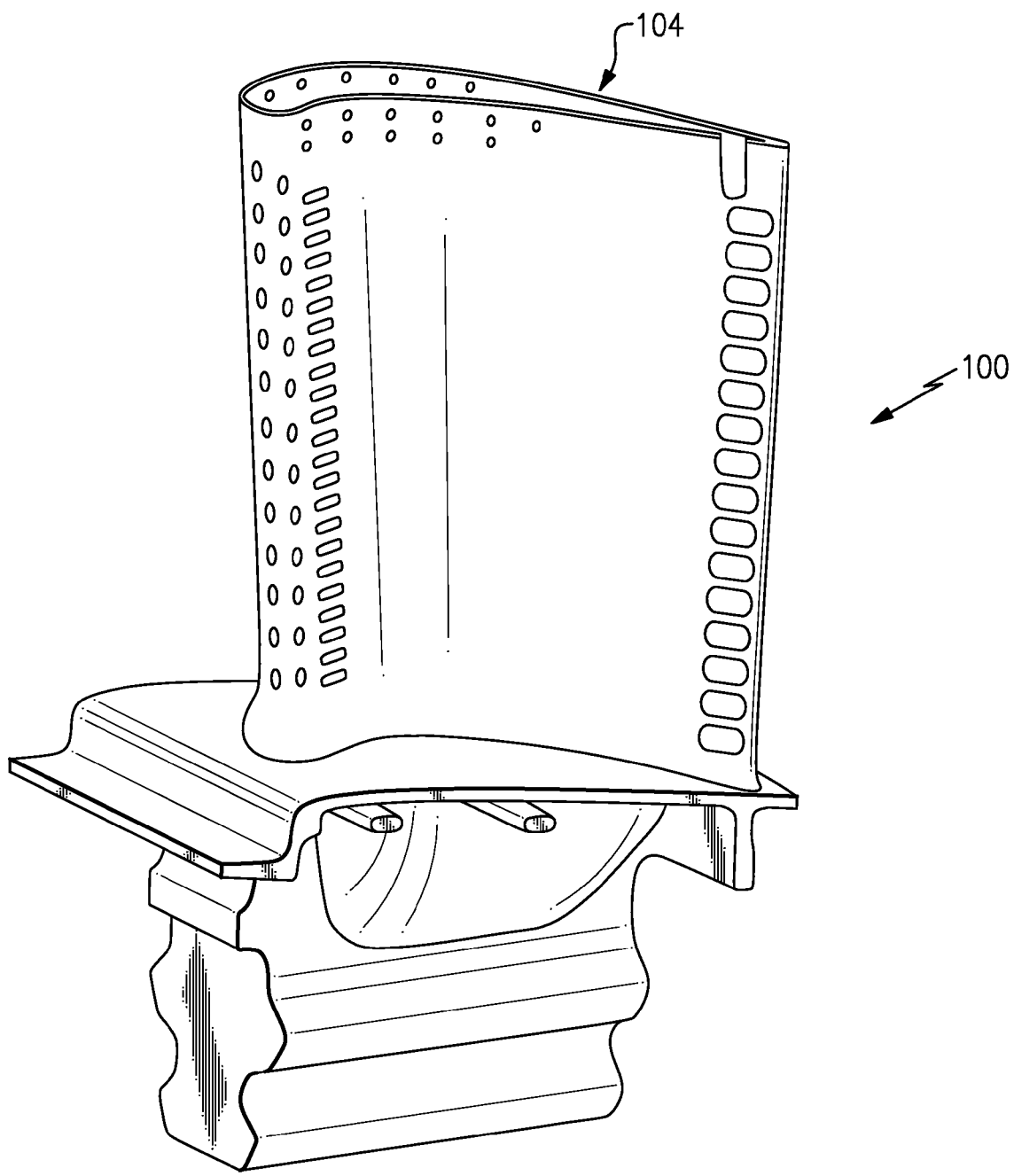
FIG. 5 shows a model of the FIG. 2 blade generated using the computed tomography scan.

Referring to FIGS. 3 to 5 with continued reference to FIG. 2, dimensioning and modeling the example blade 50 involves first inserting gage pins 70 into some or all of the cooling holes 62. A person having skill in this art and the benefit of this disclosure would understand how to select a suitable gage pin for insertion into a particular cooling hole.

The inner diameters of the gage pins 70 correspond to the diameters of the associated cooling holes 62. The diameter of the gage pins 70 corresponds to the diameter of the cooling holes 62. The orientation of the gage pins 70 corresponds to the orientation of the passages.

Gage pins 70 are used in this example. Other examples may use other types of gages, such as gage blocks.

After inserting the gage pins 70 into the cooling holes 62, a water-soluble wax 74 is applied to outer surfaces of the blade 50 in the areas holding the gage pins 70. The wax 74 is applied at a relatively low temperature (say 150° F. or 65.55° C.) and hardens to hold the gage pins 70 within the cooling holes 62. The application of the wax 74 is concentrated at the interfaces between the gage pins 70 and the blade 50.

The example blade 50 is then scanned by a computed tomography scanner assembly 78. The blade 50 is held within a moveable fixture 80 during the scanning.

The computed tomography scanner 78 includes an x-ray source 82 that projects an x-ray fan beam 86 against a detector 90. The fixture 80 and the blade 50 (with the gage pins 70 and wax 74) are moved through the fan beam 86 in various directions to scan different areas of the blade 50. The wax 74 holds the gage pins 70 during such movements. The wax 74 is removed from the blade 50 and gage pins 70 after the scanning.

A computer 94 associated with the computed tomography scanning assembly 78 captures the geometry of the blade 50 and the gage pins 70. The example computed tomography scan performed by the scanning assembly 78 is performed at a high resolution (0.25 mm spacing) and at both high and low thresholds. The high threshold scanning accurately captures the geometry of the blade 50 and the gage pins 70. The low threshold scanning allows better definition of the gage pin 70. The computed tomography scan captures portions of the gage pins 70 within the blade 50 and portions of the gage pins 70 outside the blade 50.

A controller portion 98 of the computer 94 utilizes point clouds created from the scanning assembly 78 scan of the blade 50. The controller portion 98 combines the point clouds in a modeling program to extract vector information about the cooling holes 62. The example point cloud data is collected in an .asc format file.

The controller portion 98 generates a model 100 of the blade 50 using the vector information. The model 100 includes accurately dimensioned cooling holes 104. The model 100 also includes accurately dimensioned, and oriented, cooling passages. The controller portion 98 may use a program, such as Geomagic, to filter inaccurate data from the scan. In one example, all point data associated with the blade 50 is removed from the low threshold scans, and data associated with the gage pins 70 is removed from the high threshold scans. The modified point clouds are then wrapped individually to provide an .stl file for the gage pins 70 and an .stl file for the blade 50. Both files are in the same coordinate system.

The point cloud is triangulated, which lays a 'quilt' made up of triangles over the point cloud to create a solid body. The high resolution point cloud resulting from the computed tomography scan allows for accurate wrapping of the points to create a geometrically accurate solid body. A modeling program will facilitate taking measurements from the solid body.

In terms of hardware architecture, the computer 94 can include one or more input and/or output (I/O) device interface (s) that are communicatively coupled via a local interface. The local interface can include, for example but not limited to, one or more buses and/or other wired or wireless connections. The local interface may have additional elements, which are omitted for simplicity, such as additional controllers, buffers (caches), drivers, repeaters, and receivers to enable communications. Further, the local interface may include address, control, and/or data connections to enable appropriate communications among the aforementioned components.

An example processor used within the controller portion 98 executes software code, particularly software code stored in a memory portion of the computer 98. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory portion of the computer 98 can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). The memory portion may incorporate electronic, magnetic, optical, and/or other types of storage media. Note that the memory portion can also have a distributed architecture, where various components are situated remotely from one another, but can be accessed by the processor.

The software in the memory portion may include one or more additional or separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

A feature of the disclosed example includes accurately dimensioning an aperture within a part utilizing a computed tomography scan.

The preceding description is exemplary rather than limiting in nature. Variations and modifications to the disclosed examples may become apparent to those skilled in the art that do not necessarily depart from the essence of this disclosure. Thus, the scope of legal protection given to this disclosure can only be determined by studying the following claims.

We claim:

1. A component measuring method, comprising:
   determining a position of an aperture of a component using a computed tomography scan of a gage and the component, wherein the gage is inserted into the aperture of the component during the computed tomography scan.

2. The component measuring method of claim 1, including holding the gage within the aperture using wax.

3. The component measuring method of claim 2, including applying the wax at an interface between the gage and the component.

4. The component measuring method of claim 1, including extracting vector data about the position of the aperture from the computed tomography scan.

5. The component measuring method of claim 1, wherein the aperture is a cooling hole of a turbomachine component.

6. The component measuring method of claim 5, wherein the turbomachine component is a turbomachine blade.

7. The component measuring method of claim 1, wherein the gage is a gage pin.

8. The component measuring method of claim 1, wherein the computed tomography scan scans portions of the gage within the component.

9. A component measuring method, comprising:
   inserting a plurality of gages into respective apertures of a component; and
   computed tomography scanning the gages and the component to determine the positions of the apertures.

10. The component measuring method of claim 9 including modeling the component using data from the computed tomography scanning.

11. The component measuring method of claim 9, wherein the component is a turbomachine component.

12. The component measuring method of claim 9, including holding the gages within the apertures using wax.

13. The component measuring method of claim 9, wherein the apertures are openings of passages within the component.

14. The component measuring method of claim 13, including computed tomography scanning the gages and the component to determine orientations of the passages.

15. The component measuring method of claim 9, wherein the gages comprise gage pins.

16. The component measuring method of claim 9, wherein the computed tomography scan includes scanning portions of the gages within the component.

17. A component measuring system, comprising:
a controller module that determines a position of an aperture within a component using a computed tomography scan of the component and a gage inserted into the aperture.

18. The component measuring system of claim 17, including a fixture that holds the component during the computed tomography scan.

19. The component measuring system of claim 17, wherein the aperture is a cooling hole within a turbomachine component.

20. The component measuring system of claim 17, wherein the aperture is an opening of a passage within the component and the controller module further determines an orientation of the passage.

21. The component measuring system of claim 17, wherein the gage is a gage pin.

22. The component measuring system of claim 17, wherein the computed tomography scan comprises a scan of a portion of the gage within the aperture.

* * * * *

UNITED STATES PATENT AND TRADEMARK OFFICE
CERTIFICATE OF CORRECTION

| | | |
|---|---|---|
| PATENT NO. | : 8,861,673 B2 | Page 1 of 1 |
| APPLICATION NO. | : 13/307458 | |
| DATED | : October 14, 2014 | |
| INVENTOR(S) | : Derek J. Michaels et al. | |

It is certified that error appears in the above-identified patent and that said Letters Patent is hereby corrected as shown below:

IN THE CLAIMS:

In claim 9, column 4, line 62; after determine delete "the"

Signed and Sealed this
Seventeenth Day of March, 2015

Michelle K. Lee
*Director of the United States Patent and Trademark Office*